US006475992B2

(12) United States Patent
McLean

(10) Patent No.: US 6,475,992 B2
(45) Date of Patent: *Nov. 5, 2002

(54) METHODS OF AND COMPOSITIONS FOR POTENTIATING THE ACTION OF AGENTS ACTIVE ON CELL WALL SITES OF THE SUSCEPTIBLE BACTERIA

(75) Inventor: Allan Joseph McLean, Jericho (AU)

(73) Assignee: Pharmacy and Therapeutic Advisory Consultancy Pty LTD, Melbourne (AU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/117,105

(22) PCT Filed: Jan. 24, 1997

(86) PCT No.: PCT/AU97/00040
§ 371 (c)(1),
(2), (4) Date: Aug. 26, 1998

(87) PCT Pub. No.: WO97/26886
PCT Pub. Date: Jul. 31, 1997

(65) Prior Publication Data
US 2002/0049171 A1 Apr. 25, 2002

(51) Int. Cl.$^7$ .......................... A01N 43/04; A61K 31/70
(52) U.S. Cl. ........................... 514/37; 514/36; 514/38; 514/39; 536/4.1; 536/13.6; 536/16.8
(58) Field of Search ............... 536/13.6, 16.8, 536/4.1; 514/36–42

(56) References Cited

U.S. PATENT DOCUMENTS 3,644,616 A  2/1972  Konopka et al. .............. 424/14
5,523,288 A  6/1996  Cohen et al. .................. 514/12

FOREIGN PATENT DOCUMENTS

GB  1 400 464   7/1975
WO  93/01818   2/1993
WO  95/12406   5/1995

OTHER PUBLICATIONS

Hooton et al., Proc. Int. Cong. Chemotherapy, vol. 9, (abstract–pp. 84/8–84/11).*
Hooten et al., Proc. Int. Cong. Chemotherapy, 13, vol. 9, pp. 84/8–84/11 (abstract), 1993.*
Allan et al., Antimicrobial Agents and Chemotherapy, vol. 27(5), pp. 782–790, 1985.*
Scaglione et al., Chemotherapy, vol. 41, pp. 239–246, 1995.*
Antimicrobial Agents and Chemotherapy, vol. 36, No. 12, 1992, McGrath et al.: "Pharmacodynamics of one–daily amikacin in various combinations . . . "; pp. 2741–2746.
The Journal of Clinical Pharmacology, vol. 26, No. 8, 1986; Keller et al.: "Aminoglycoside dosate in hemodialysis patients"; pp. 690–695.
Antimicrobial Agents and Chemotherapy, vol. 39, No. 1, 1995; Barclay et al.: "Improved efficacy with nonsimultaneous administration of first does of gentamicin . . . "pp. 132–136.
The Journal of Infectious Diseases, vol. 165, No. 2, 1992; Vergeres et al.: "Amikacin, ceftazzidime, and flucloxacillin against suspended and adherent pseudomonas . . . "pp. 281–289.
Derwent Abst. Accession No. 90–017182/03—Nov. 28, 1989.
Patent Abstracts of Japan, C–49, p. 17 JP 54/046840 A (Sangyo Kagaku Kenkyu Kyokai, Apr. 13, 1979.
The Journal of Infectious Diseases, vol. 165, No. 4, 1992; Bryant et al.: "β–lactam enhancement of aminoglycoside activity under conditions of reduced pH and oxygen tension that may exist in . . . " pp. 676–682.
Diagnostic Microbiology and Infectious Disease, vol. 19, No. 1, 1994; Laverdiere, M. "in vitro synergism of ceftriaxone combined with aminoglycosides against pseudomonas aeruginosa", pp. 39 and 46.
Chemotherapy, vol. 41, No. 4, 1995; Scaglione et al: "Bacterial kinetics of an in virto infection model of once–daily ceftraxone . . . "; pp. 239–246.
The Journal of Infectious Diseases, vol. 169, No. 6, 1994; Mainardi et al.: "Activity of isepamicin and selection of permeability mutants to β–lactams during aminoglycoside therapy of experimental endocarditis due to . . . " pp. 1318–1324.
The Journal of Antimicrobial Chemotherapy, vol. 36, Suppl. A, 1995; Schuler et al.: "Safety and efficacy of meropenem in hospitalised children: randomised comparison with cefotaxime, . . . " pp. 99–108.
Wagenvoort et al., "Bactericidal Effect of Combinations of Cephalosporins with Tobramycin on Clinical Isolates...", Arzneim–Forsch. / Drug Res. 36 (II), Nr. 9 (1986).
Weinstein et al., "Cephalosporin–Aminoglycoside Synergism in Experimental Enterococcal Endocarditis", Antimicrobial Agents and Chemotherapy, Jun. 1976, pp. 983–987.
Hyams et al., "Synergy Between Cephalosporin and Aminoglycoside Antibiotics Againt Providencia and Proteus", Antimicrobial Agents Chemotherapy, Jun. 1974, pp. 571–577.

(List continued on next page.)

Primary Examiner—Johann Richter
Assistant Examiner—Howard V. Owens, Jr.
(74) Attorney, Agent, or Firm—Larson & Taylor PLC

(57) ABSTRACT

The invention provides a method of potentiating the activity of antibacterial agents that act on bacterial cell walls, comprising the step of administering to a subject an antibacterial agent and an aminoglycoside to attain a peak concentration of at least 4 mg/l of aminoglycoside and thereafter maintaining the aminoglycoside at a concentration of up to 4 mg/l for at least 1 hour. Compositions comprising an antibacterial agent and an aminoglycoside for efficacious treatment of bacterial infection are also provided.

12 Claims, 6 Drawing Sheets

OTHER PUBLICATIONS

Fekety et al., "Antibiotic Symergism: Enhanced Susceptibility of Enterococci to Combinations of Streptomycin and Penicillins or Cephalosporins", Antimicrobial Agents and Chemotherapy, 1996, pp. 156–164.

Van De Auwera, "Interaction of gentamicin, dibekacin, netilmicia and amikacin with various penicillins,..." Journal of Antimicrobial Chemotherapy, (1985), 16, pp. 581–587.

Bayer et al., "Enhanced In Vitro Bactericidal Activity of Amikacin of Gentamicin Combined with Three New Extended–Spectrum...", Antimicrobial Agents and Chemotherapy, Jun. 1984, pp. 725–728.

Hallander et al., "Synergism Between Aminoglycosides and Cephalosporins with Antipseudomonal Activity...", Antimicrobial Agents and Chemotherapy, Nov. 1982, pp. 743–752.

Markowitz et al., "Comparative Susceptibilities of Clinical Isolates of Serratia marcescens to Newer Cephalosporins,...", Antimicrobial Agents and Chemotherapy, Nov. 1980, pp. 651–656.

Fu et al., "A Comparative Study of the Activity of Cefamandole and Other Cephalosporins and Analysis of the...", The Journal of Infectious Diseases, vol. 137, Supplement, May 1978, pp. S38–S48.

* cited by examiner

METHODS OF AND COMPOSITIONS FOR POTENTIATING THE ACTION OF AGENTS ACTIVE ON CELL WALL SITES OF THE SUSCEPTIBLE BACTERIA

The present invention relates to a method of potentiating the activity of an antibacterial agent by using an aminoglycoside, and to novel compositions comprising an antibacterial agent and an aminoglycoside. It also relates to a method of treating bacterial infection by administration of the composition of the invention. More particularly, the invention relates to the use of an aminoglycoside to potentiate the activity of antibacterial agents acting at or near cell wall sites, such as β-lactams or cephalosporins. The invention also contemplates optimisation of the efficacy of aminoglycosides.

BACKGROUND OF THE INVENTION

A major problem in treatment of infections caused by bacteria, particularly hospital acquired infections, is that an increasing number of bacteria are becoming resistant to antibiotics. For example, many strains of Staphylococcus and Enterococcus are now resistant to most of the currently-available antibiotics. Other organisms, such as Pseudomonas, respond poorly. This problem is exacerbated by the ability of many bacteria to transfer resistance to other species of bacteria.

In laboratory testing, this manifests itself as a requirement for concentrations of antibiotics which are higher than the reported minimum inhibitory concentration (MIC) to inhibit the growth of the organisms.

One group of antibiotics which are clinically becoming less useful due to acquired resistance are the cephalosporins. Cephalosporins are conventionally believed to act at surface sites on the bacterial cell wall at or near the enzymes responsible for cell wall synthesis. In Gram-negative organisms with an outer cell wall, the action of cephalosporins is limited by access to these surface sites in the inner cell wall because of molecular size and other determinants of ability to penetrate porin structures in the outer cell wall, and by the action of enzymes (cephalosporinases) which break down the cephalosporins. These cephalosporinases are largely responsible for the emerging clinical resistance of bacteria to cephalosporins.

Although aminoglycoside antibiotics are active against a wide spectrum of organisms, their use has been severely limited by the toxic side effects which occur at the doses required to achieve the desired antibacterial effect.

Thus, there is a need to improve the efficacy of antibiotics, particularly cephalosporins. Three is also a need to reduce the toxicity of aminoglycoside antibiotics, particularly gentamicin.

It has conventionally been thought that aminoglycosides exert their antibacterial effects via a strictly intracellular mechanism involving inhibition of ribosomal activity. However, the present inventor has examined data on uptake of radioactively—labelled aminoglycosides, and now proposes that aminoglycosides also act at the cell surface so as to contribute to the process of entry into the cell. Thus the hypothesis underlying the present invention is that an important part of the action(s) of aminoglycoside antimicrobials involve creation of breaches in external cell walls of bacteria and in other external capsular layers or membranes composed of lipopolysaccharide or mucopolysaccharide constituents.

It was thought
1. that the exposure profiles necessary for this action of aminoglycosides were likely to differ from the concentration-time profiles found to apply to intracellular effect(s), and that novel exposure profiles might be identified which would allow avoidance of toxicity on mammalian systems;
2. that the breaches in external cell walls and capsular membranes and layers of bacteria could facilitate entry and access to sites of action of other antibiotics such as cephalosporins which acted at or near cell surfaces, and additionally, that enzyme degradation of antibiotics (e.g. cephalosporinases) might be by-passed.

It has now been surprisingly found that the activity of β-lactam antibiotics, including cephalosporins, can be potentiated by the use of a non-toxic amount of an aminoglycoside antibiotic.

The studies detailed herein, using gentamicin and tobramycin demonstrate that the concentration-time profiles producing the cell surface effect involve relatively prolonged exposures over many hours, at lower concentrations than those normally used clinically, where rapid onset (bolus) of high concentration exposure has been the characteristic approach to clinical dosing.

The potentiation of cephalosporin action by degrees in excess of 100 fold was also a surprising finding and suggests the efficiency of cell wall porin as exclusion barriers and the enzymatic (cephalosporinase) destruction of cephalosporins.

BRIEF DESCRIPTION OF THE INVENTION

In one aspect, the invention provides a method of potentiating the activity of an antibacterial agent active on bacterial cell wall, comprising the step of administering to a subject in need of such treatment said antibacterial agent and an aminoglycoside in an amount effective to attain a peak concentration of at least 4 mg/l of the aminoglycoside, and thereafter maintaining the aminoglycoside at a concentration of up to 4 mg/l for at least 1 hour.

Preferably, the antibacterial agent is active on bacterial cell wall and acts at or near the cell wall of the bacteria. Thus, the invention provides a novel action of an aminoglycoside at cell surfaces which results in the potentiation of the effect of one or more antibiotics acting at or near bacterial cell wall or sites thereof.

Preferably, the antibacterial agent is a β-lactam and most preferably, a cephalosporin or cephamycin.

The aminoglycoside is most preferably gentamicin or tobramycin.

In a preferred embodiment, the activity of cephalosporin is potentiated by administering to a subject an amount of gentamicin or tobramycin effective to produce a peak concentration of up to 18 mg/l plasma. This may be achieved by administration of 70–280 mg (1–4 mg/kg body weight) over 1–2 hours. Thereafter, the aminoglycoside is administered preferably at 5–20 mg/hr for 4–12 hours to maintain a plasma concentration of 1–4 mg/l. The aminoglycoside may further be maintained at a concentration of 1.0 mg/l plasma or less up to 24 hours.

Desirably, 300 mg of cephazolin as a specific example is administered over 24 hours, maintaining a plasma concentration at 2 mg/ml or more.

In a particularly preferred embodiment, the cell wall active antibacterial agent is at 2 mg/ml when the aminoglycoside is maintained at 1–4 mg/l, and for a further 8–24 hours thereafter.

The method of the invention thus provides a critical profile of aminoglycoside exposure in the animal or human body which is necessary for optimisation of the action of aminoglycoside(s), but more particularly, for the potentiation of one or more other antibiotics. This also allows the avoidance and/or minimisation of the known clinical toxic effects of aminoglycosides on hearing, posture and dynamic balance. The profile is achieved by taking account of transfer of antibiotics from blood to tissues. However, provision is made in the method such that the antibiotic concentrations in the inner ear (vestibular apparatus and organ of Corti) do not achieve concentrations known to be toxic, and to prevent those toxic concentrations from being present for periods of time known to be necessary for toxic effects to develop. (McLean A J, Ioannides-Demos L L, Spicer W J, Christophidis N, "Aminoglycoside dosing: one, two or three times a day?", Med J Aust. 164:39–42, 1996).

The peak concentrations of aminoglycoside which are most desirable are 4–18 mg/l, and are preferably maintained at a minimum of 1–4 mg/l, depending on bacterial sensitivity as evidenced by MIC testing. Maintainance of this level would require a mass of some 5–15 mg per hour of gentamicin to be delivered to the circulation of an average patient at a uniform rate, although variations will be required as a result of differing body size, renal function and various disease conditions (McLean et al 1996, supra). The rate and amount of active agent to be delivered can be determined easily by a person skilled in the art.

In accordance with existing formulation protocols, such exposure would presuppose intramuscular administration of a mixture of depot formulation. However, recent developments would allow for intravenous or oral formulations. Such formulations would need to deliver initial profiles as described above (4–18 mg/l), then allow for maintainance of concentrations at 1–4 mg/l for specific periods of time. Following this, lower levels of aminoglycoside and cephalosporin may be maintained for about 8 hours onwards. In one specific embodiment of the formulation, ongoing concentrations of aminoglycoside in the circulation should not exceed about 1 mg/l at about 8–16 hours after administration of the formulation, so as to prevent toxic levels of aminoglycoside accumulating in the inner ear and kidney.

The method of the invention also allows the effective dose of the antibacterial agent which is potentiated to be reduced. This again allows toxic effects to be negated or avoided.

The method of the invention allows the development of a pharmaceutical formulation of cephalosporins such as cephazolin which are clinically effective at ⅙ to ⅓ of the current clinical doses. Physical tolerance would be enhanced markedly so that intramuscular formulations can be realistically used and tolerated. However, advances in formulation should allow the development of intravenous or oral formulations to deliver greatly reduced concentrations of the drug required as a result of the aminoglycoside potentiation.

Thus, in a second aspect, the invention provides an antibacterial composition comprising an aminoglycoside and an antibacterial agent active on bacterial cell wall, said composition formulated thereby to attain a peak concentration of at least 4 mg/l aminoglycoside which is thereafter maintained at a concentration of up to 4 mg/l for at least 1 hour following administration to a subject in need of such treatment so as to potentiate the activity of said antibacterial agent.

In a third aspect, the invention provides a method of treating bacterial infection, comprising the step of administering to a subject an antibacterial agent active on bacterial cell wall together with an aminoglycoside to attain a peak concentration of at least 4 mg/l of aminoglycoside and thereafter maintaining the aminoglycoside at a concentration of up to 4 mg/l for at least 1 hour; wherein said aminoglycoside potentiates the activity of said antibacterial agent.

The compositions of the invention may comprise a cephalosporin and an aminoglycoside in dosage-unit form and optionally, in admixture with a conventional, pharmaceutically acceptable carrier suitable for administration to a clinical or home patient by intramuscular, subcutaneous, intravenous, oral or rectal administration. The relative proportions of aminoglycoside and other antibiotics to be delivered can be determined without undue experimentation by a person skilled in the art and in view of the teachings herein.

Preferably, the compositions of the invention would allow once-a-day administration of antibiotics either in hospital or at home.

The method and composition of the invention may be used in the treatment of infection by Gram-negative, Gram-positive bacteria or mycobacteria. Other conditions include but are not limited to surgical chemoprophylaxis, and focal or systemic sepsis.

The aminoglycosides other than gentamicin which share its mechanisms of action and are comprehended by this invention include: tobramycin, netilimicin, amikacin and streptomycin.

The agents directly related to cephazolin and sharing the potentiating mechanisms directly are cephalosporins and cephamycins, as exemplified by but not limited to the following: cephalosporin, cephalothin, cephaloridine, cephalexin, cephaglycin, cephradine, cefaclor, cefoxitin, cefamandole, cefotaxime, ceftriaxone, ceftazidime and cefotetan.

The cephalosporin dosage required for this invention is far lower than has been used before, specifically 0.166–0.33 g versus 1 g current minimum standard dose (Cahn M M et al, "Comparative serum levels and urinary recovery of cephazolin, cephalosporin and cephalothin in human", J. Clin. Pharmacol. 14:61–66, 1974).

Agents known generically as β-lactam antibiotics share mechanisms with cephazolin, and constitute the various penicillin groups and monobactams. Examples include the following: penicillin G, ampicillin, methicillin, flucloxacillin, carbenicillin, ticarcillin, piperacillin, imipenin.

Other agents which will benefit because of improved access to sites of action include diverse agents exemplified by: bacitracin, chloramphenicol, macrolides such as erythromycin, clarithromycin, rifampicin, vancomycin, quinolonem antibiotics such as nalidixic acid, norfloxacin, cycloserine and metronidazole.

The organisms amenable to therapy by way of the various combinations include a wide variety of Gram-positive and Gram-negative organisms with a variety of growth circumstances and requirements ranging from aerobic to anaerobic growth, including:

(a) Gram-positive bacteria such as *Strep.pyogenes* (Group A), *Strep.pneumoniae, Strep.GpB, Strep.viridans, Strep.GpD* -(Enterococcus), *Strep.GpC* and *GpG, Staph.aureus, Staph.epidermidis, Listeria monocytogenes, Anaerobic cocci, Clostridium spp.*, and *Actinomyces spp;* and (b) Gram-negative bacteria such as *Escherichia coli, Enterobacter aerogenes, Kiebsiella pneumoniae, Proteus mirabilis, Proteus vulgaris, Morganella morganii, Providencia stuartii, Serratia marcescens, Citrobacter freundii, Salmonella typhi, Salmonella paratyphi, Salmonella typhi murium, Shigella spp., Yersinia enterocolitica, Acinetobacter calcoaceticus, Flavobacterium spp., Haemophilus influenzae, Pseudomonas aueroginosa, Campylobacter jejuni, Vibrio*

*parahaemolyticus, Brucella spp., Neisseria meningitidis, Neisseria gonorrhoea, Bacteroides fragilis,* and *Fusobacterium spp.* and as well as other organisms such as *Mycobacterium tuberculosis, Mycobaterium smegmatis* and other Mycobacteria.

Selected antibiotic combinations may be used in accordance with the invention in the following clinical conditions:

(a) Surgical chemoprophylaxis such as: ear, nose and throat surgery (otolaryngology); genitourinary surgery; contaminated penetrating injuries of the skin; compound fractures; bite wounds; penetrating eye injuries; abdominal surgery; acute cholecystitis; perforated viscus; peritonitis with cirrhosis; and dental chemoprophylaxis; and (b) Focal and systemic sepsis such as: bacterial endocarditis; empirical therapy of systemic sepsis; skin cellulitis; decubitis, ischaemic and diabetic ulcers; severe or hospital-acquired, or institutional pneumonia; urinary infection; febrile neutropaenia; prostatitis; epididymo-orchitis; suppurative wound infections; gangrene; osteomyelitis; and pulmonary tuberculosis (for streptomycin combinations according to the infection).

In a further aspect, the invention involves the administration in specified ways of an aminoglycoside(s) to optimise the action of the aminoglycoside alone and to potentiate the action of one or more antibiotic agents which act at or near cell wall sites of bacterial cells.

When cephalosporins are placed in culture medium containing susceptible bacteria, cephalosporin diffuses down the concentration gradient existing between the concentration in the culture medium and the concentration at the sites of action on the bacterial cell wall. The action of cephalosporinases chemically degrades and inactivates the cephalosporin such that there are limitations on the degree of inhibition of growth of the bacteria.

In comparative experiments described in the examples herein, a reference strain of *Escherichi coli (E. coli* NCTC 10418) was exposed to constant concentrations of cephazolin in the culture medium (see FIG. 1A and 2A). As these concentrations were varied, the growth of the bacterial culture was changed. At the lowest concentration of cephazolin (1.0 mg/l) the growth of the culture was delayed in relation to control (see FIG. 1B). As concentrations in the medium were increased, there was a major decline in numbers and a delay in regrowth.

However, it was not possible to produce a complete kill or eradication of *E.coli* NCTC 10418 using cephalosporin alone. The organisms in the media were able to maintain their numbers in a reduced state even in the continuing presence of cephazolin. This outcome is due to the exclusion of cephalosporins by porin channels in the outer cell wall and to the action of cephalosporinase which keeps cephazolin levels below that required for full bactericidal effect.

DETAILED DESCRIPTION OF THE INVENTION

The invention will now be described in detail by way of reference only to the following non-limiting examples, and to the figures. The complete data shown graphically in FIGS. 1, 2 and 3 are contained in Tables 1, 2 and 3.

While a representative microorganism, *E. coli*, a representative aminoglycoside antibiotic (gentamicin) and a representative cephalosporin (cephazolin) were studied herein to generate the majority of data presented, it will be clearly understood that the invention is not limited to this microorganism or to these specific agents.

EXAMPLE 1

Antibacterial Action of Aminoglycoside and Cephalosporin on *E. coli* Cultures The experimental work described herein involved testing bacterial response while changing aminoglycoside concentrations with time in the test tube, and mimics closely measurements made in man under clinical conditions (Bastone E B, Li S C, Ioannides-Demos L L, Spicer J, McLean A J, "Kill kinetics and regrowth patterns of *E. coli* exposed to gentamicin concentration-time profiles simulating in vivo bolus or infusion dosing", Antimicrob Agents Chemother. 37:914–917, 1993).

With each antibiotic, concentration-time profiles similar to those observed in the blood of clinical patients following conventional intravenous dosing of an aminoglycoside (gentamicin) and pump-driven profiles of gentamicin and cephalosporin (cephazolin) were attained. The concentration-time profiles for each drug class have the general form shown in FIG. 1A and FIG. 3A of the accompanying drawings. Additionally a gentamicin profile of the form shown in FIG. 3A was generated, which reached a peak of 12 mg/l over 3 hours, was maintained at 12 mg/l for a further hour, then was reconstituted to a range of steady-state concentrations (0, 0.5, 1.0, 2.0, 3.0, 4.0 mg/l) to yield the experimental results shown in Table 4.

Figure 1A:
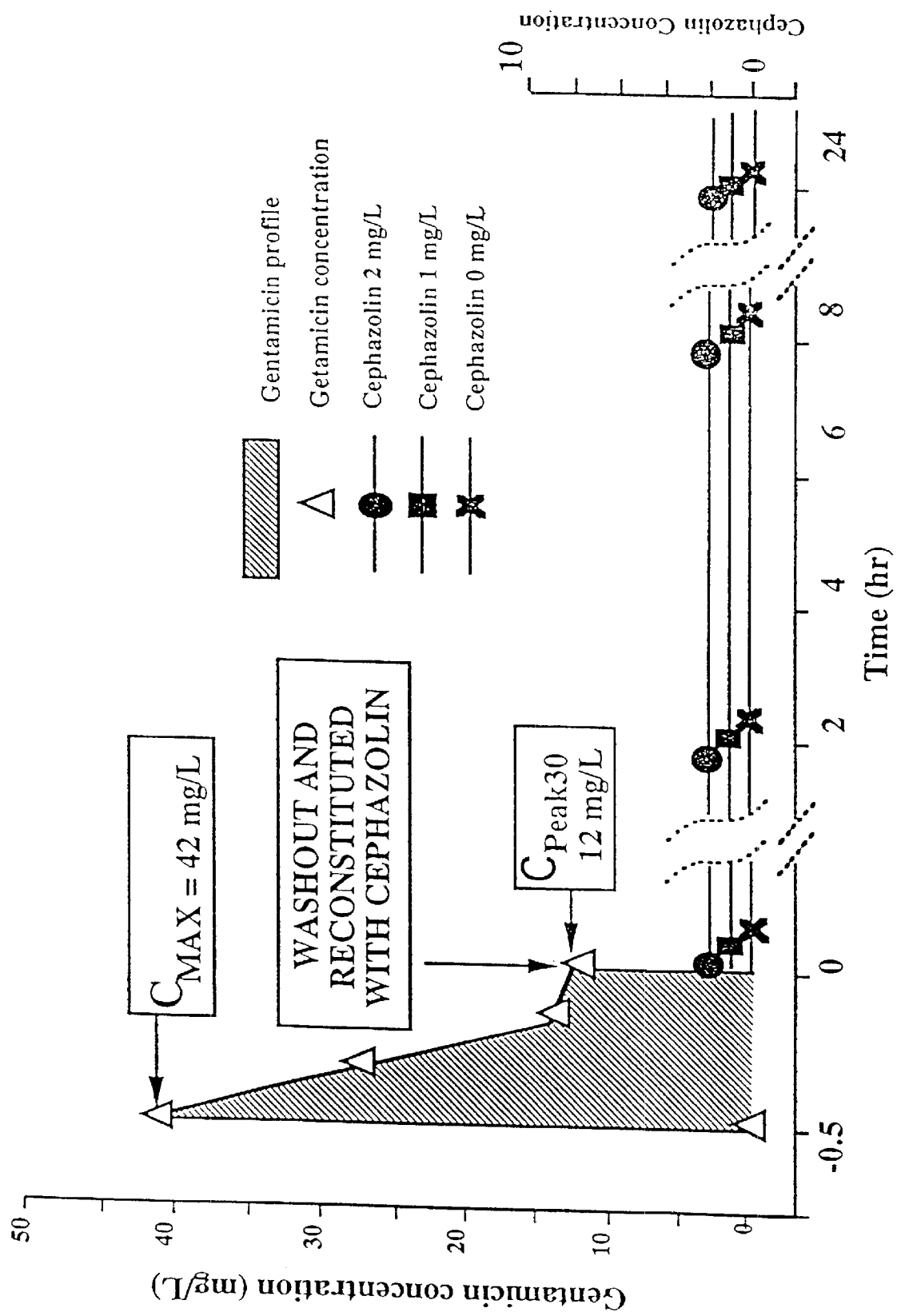
FIG. 1 shows the time-concentration profile of gentamicin after exposure of a culture of *E. coli* to a bolus of the aminoglycoside (1A) and the antibacterial action of a constant amount of different levels of cephazolin added 30 minutes after the bolus and removal of the gentamicin by centrifugation of culture medium at Time=0 (1B).

As shown FIG. 1A, the pre-exposure to gentamicin provides a model of an in vivo bolus which generates a transient peak (C max) of 42 mg/L followed by a decrease over 30 minutes to 12 mg/L (C peak 30). The form of this profile is governed in vivo by distribution into tissue from the central circulation. In in vitro experiments, gentamicin was removed (T=0 time) by centrifugation and washing with antibiotic-free medium. The incubation was reconstituted with media containing 0 mg/l, 1 mg/l or 2 mg/l cephazolin (see FIG. 1A).

Figure 1B:
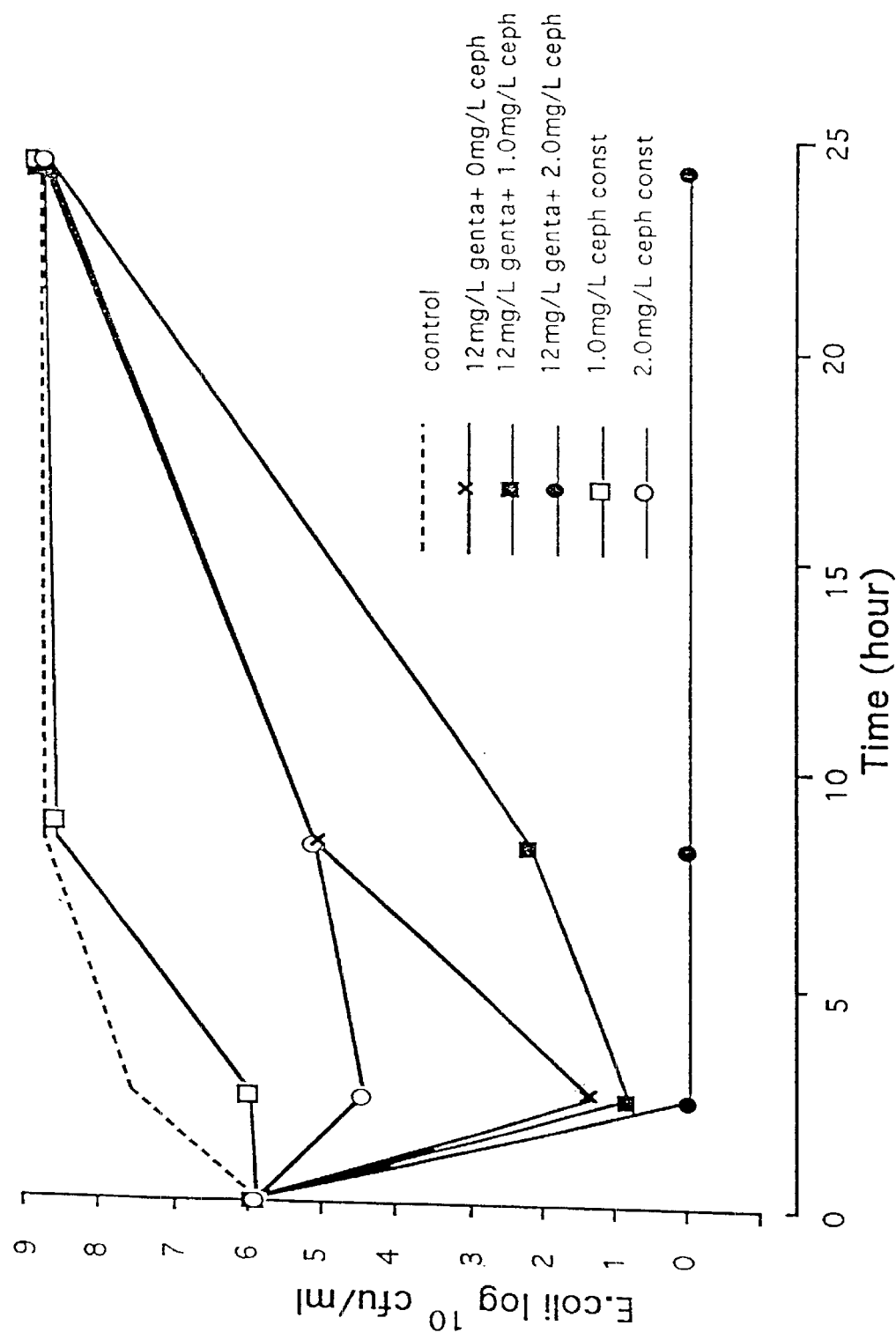

The quantitative influence of antibiotic exposure on bacterial growth is detailed in Table 1, and illustrated diagrammatically in FIG. 1B. The figure shows the number of colonies of *E.coli* which grew on microbiological culture plates when samples of the broth culture were taken at standard times throughout the antibiotic exposure regimens (FIG. 1A).

In FIG. 1B, it can be seen that the pattern of growth of control organisms (not exposed to antibiotic) is designated by the dotted line ( . . . ), while the growth patterns of test organisms are represented by the solid lines with symbols indicating each type of treatment or test (FIG. 1B). Colony numbers declined initially to 2 h (due to bactericidal effect), then a variable pattern and degree of recovery followed. The treatment with gentamicin alone, or combined with cephalosporin, resulted in the greatest decline in numbers and slow or no recovery. Pretreatment with gentamicin (C peak 30=12 mg/l) followed by maintained concentrations of 2.0 mg/l cephazolin (see FIG. 1A) resulted in complete kill (see FIG. 1B) or eradication of the *E. coli.*

Figure 2A:
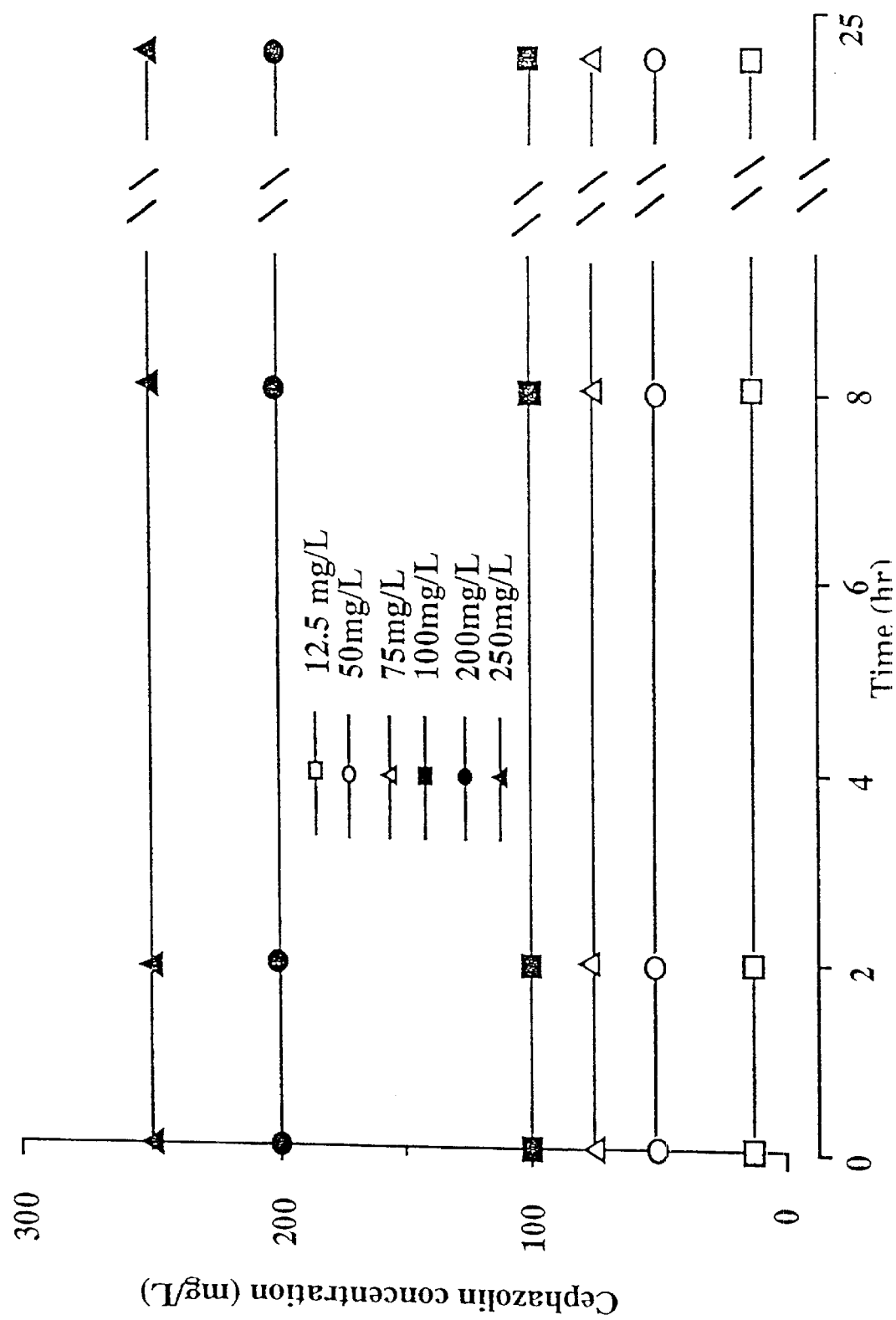
FIG. 2 shows the antibacterial action of cephazolin on *E. coli* (2B) following exposure of colonies to different concentrations of the antibacterial agent (2A).
Figure 2B:
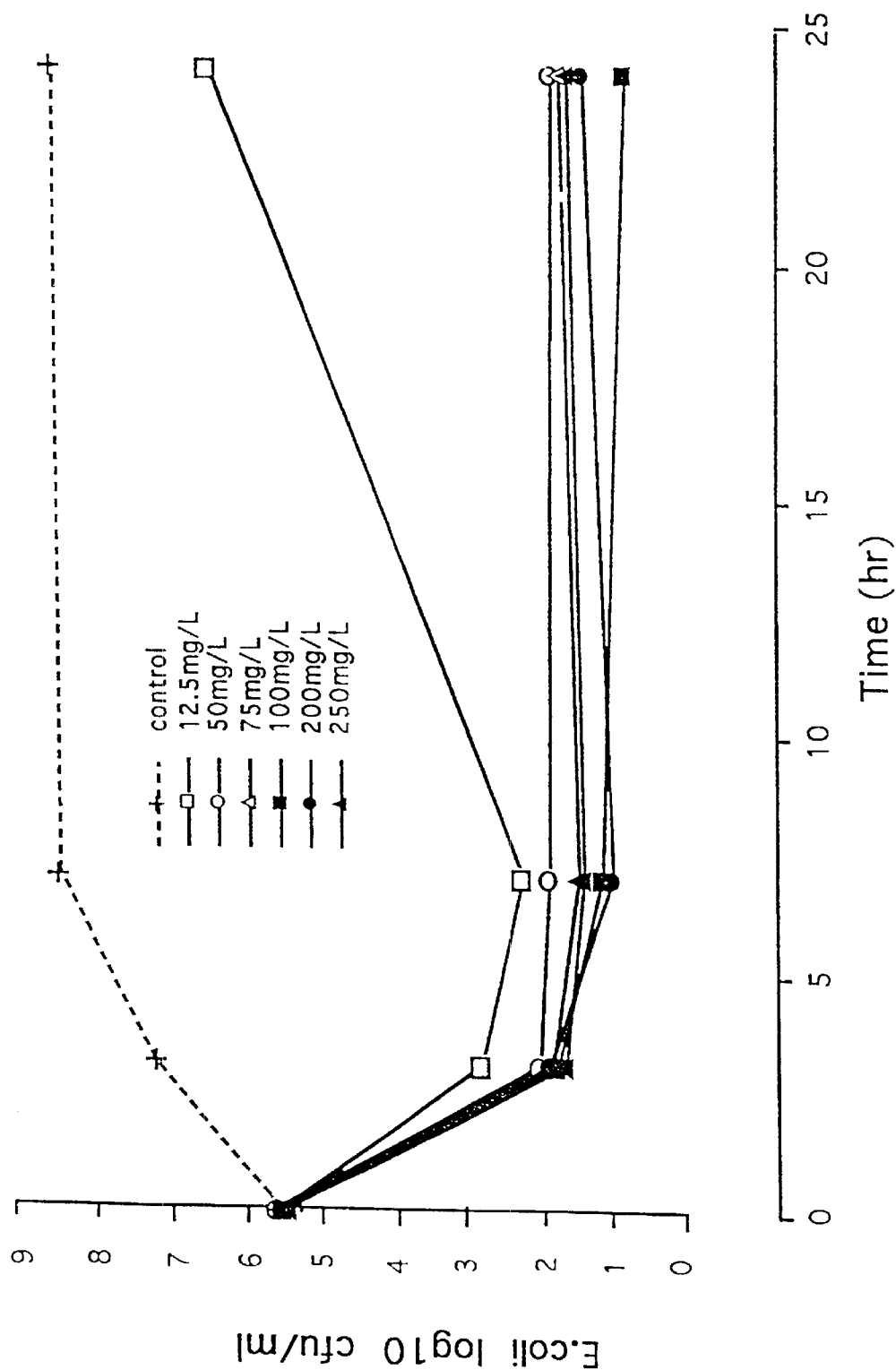

These results are in marked contrast to the findings with exposures to constant concentrations of cephalosporin alone (FIG. 2A), tested over a very wide range of levels up to 250 mg/l (see FIG. 2A). The cephalosporin effect reached a maximum when *E. coli* growth was reduced to 10 colony forming units(cfu)/ml (see FIG. 2B).

The data reflect an approximately 200-fold increase in the activity of standard cephalosporins as a result of administration or exposure of this antibiotic in a specific manner i.e. constant concentrations for lengths of time in combination with highly specific and novel profiles of gentamicin.

Without wishing to be bound by any proposed mechanism for the observed advantages of the invention, the novel action of aminoglycoside reported herein can be explained by at least two possible underlying mechanisms of action. The first possibility is the creation of new channels in the external membrane(s) allowing facilitated access of cephalosporin to the sites of cephalosporin action, such new channels resulting in reduced exposure of the cephalosporin to cephalosporinases. The alternative explanation, considered to be less likely, is that the profile of aminoglycoside exposure in terms of both concentration and time results from direct inhibition of the cephalosporinases present in the normal porin pathways and located at or near the cephalosporin binding sites, thus resulting in potentiation of the action of cephalosporin.

It is believed that cephalosporins act on the structural cell wall and create "holes" for entry of agents such as aminoglycosides which act inside the cell. In contrast, aminoglycosides are believed to make initial minor breaches across the outer wall, then pass through these breaches, cross the inner wall and cell membrane to act predominantly intracellularly on 30S ribosomes and related structures within the cell and thus inhibit general cell metabolism, including cell wall synthesis. Despite indications of a surface cell wall action, it has been and currently is generally accepted that the major action of aminoglycosides is inside the cell.

A capacity for an aminoglycoside to facilitate access of a cephalosporin to its surface site of action is evidenced by the potentiation of the effect of cephazolin as reported herein. The invention therefore contemplates administration of a combination of an aminoglycoside and a surface-acting antimicrobial (e.g. cephalosporin).

Figure 3A:
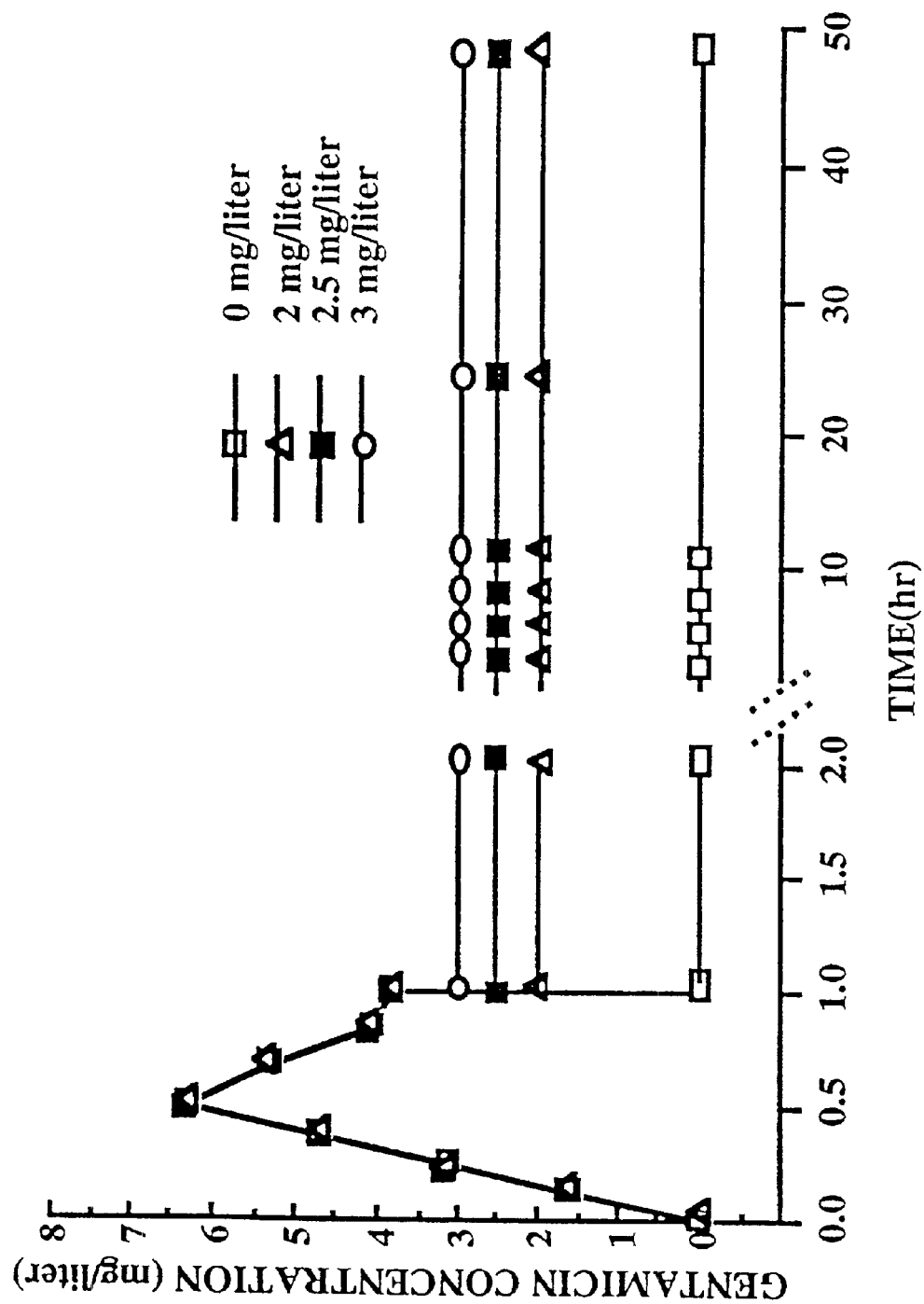
FIG. 3 shows the time-concentration profile of gentamicin (3A) and *E. coli* counts (3B) following exposure to the aminoglycoside. The aminoglycoside reached a peak concentration of 4 mg/l 30 minutes post-dose and was removed from the *E. coli* culture by washing. Medium containing 0, 2, 2.5 and 3 mg/l gentamicin was reconstituted and added to the culture at 1 hour after initial exposure to the aminoglycoside (n=6).

Regardless of the exact mechanism which might be finally determined, the observations allow radical redesign of aminoglycoside and cephalosporin formulations either alone or as combination formulations. The aminoglycoside profile will be one of two types, depending on the clinical circumstances. When the setting is of serious illness and the therapeutically targeted organisms are in the blood-stream, the aminoglycoside profile indicated is shown in FIG. 1A. In contrast, where the infection is tissue based, the exposure required is a maintained profile of aminoglycoside as illustrated in FIG. 3A.

Figure 3B:
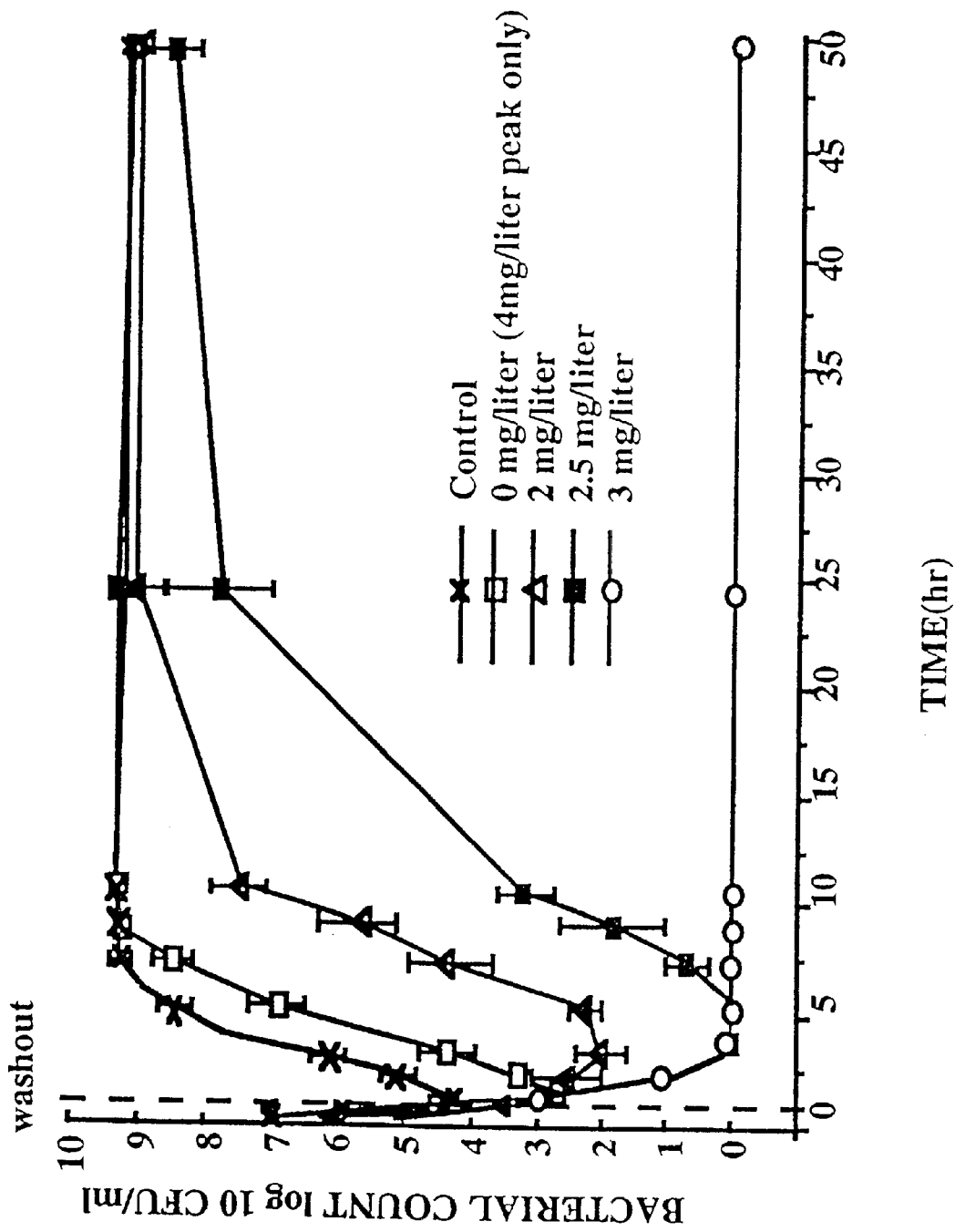

For aminoglycosides, totally novel information is also represented by the data in Table 3 and Table 4. The studies here revealed both a desirable concentration requirement (in this case a peak requirement of 4–12 mg/l and a maintained concentration requirement of 1.0–4.0 mg/l) and a particularly preferred time requirement of 4–8 hours. This group of data together produce a paradigm shift in response pattern compared to lower concentrations e.g. 2.5 mg/l (see FIG. 3B and Bastone et al, 1993, supra).

The cephalosporin profile is preferably a constant concentration of 2 mg/l or above, depending on the relative resistance of the target pathogen to the combination of aminoglycoside/cephalosporin. The type of formulation which could be applied in the first instance is that normally used for intramuscular administration of cephalosporin. Formulations for oral or intravenous use can be developed by a person skilled in the art without difficulty with the aim of maintaining the required minimum concentrations.

The time boundaries for maintained exposures with aminoglycoside may be 1.0–16 hours, while the required maintained concentrations will be a function of the resistance of the organism as determined by the minimum inhibitory concentration (MIC) of the pathogen isolated in culture and time-concentration requirements of the organism(s) being treated. For *E. coli* NCTC 10418 described herein, the maintained concentration/MIC ratio required for gentamicin was demonstrated to be 6:1, while the ratio for cephazolin (in the presence of gentamicin) was 2:1. In contrast, resistant Pseudomonas organisms required peak concentrations of 18 mg/l, while the ratio of maintained concentration:MIC was 0.5.

EXAMPLE 2

Effect of Tobramycin and Cephalosporin on Pseudomonas

The range of aminoglycoside antibiotics was extended to include tobramycin, the bacterial species type was extended from Enterobacteriaceae to Pseudomonacea, and the organism response range broadened to include an antibiotic resistant strain in Pseudomonas studies.

We have established the principles of the required degree and pattern of alteration in drug delivery requirement with variation in MIC from studies of a reference strain of *Pseudomonas aeruginosa*, ATCC27853 (MIC=1 mg/l), and an antibiotic resistant strain of this organism (MIC=2–4 mg/l), isolated from a clinical patient.

The reference strain was killed by a tobramycin profile with initial patterns of the type shown in FIG. IIIA but with a concentration of 8 mg/l at 1 hour, reducing systematically until 8.5 hr when a fixed concentration of 0.8 mg/l for 16 hours resulted in complete kill. In contrast, the resistant clinical strain required a peak concentration of 18 mg/l combined with a maintained level of 1 mg/l.

Route of Administration

Intramuscular dosing is possible with the doses of cephalosporin and aminoglycoside contemplated by the invention because of the smaller volumes and hence better physical tolerance of the injection (currently a limiting factor). However, technological advances will allow formulations of both aminoglycoside and cephalosporin capable of providing the required profiles according to the invention to be generated by oral or intravenous dosing (Bakker-Woudenberg et al. J. Inf. Dis. 171: 938–947, 1995, Vincente et al, JAC 28: 269–271, 1990).

Other Embodiments of the Invention

In one embodiment, there is provided a method of using gentamicin or other aminoglycoside(s) in potentiating the action of a cephalosporin(s) or other antibacterial agent(s) acting at or near cell wall sites on pathogenic bacteria in the treatment of pathogenic bacterial infections in animals, particularly in the treatment of Gram-negative pathogenic bacterial infections in human patients, by administering to the animal or patient, either separately or together, the gentamicin or other aminoglycoside(s) and the cephalosporin(s) or other antibacterial agent(s) acting at or near cell wall sites on pathogenic bacteria, such that:

(i) the concentration of gentamicin or other aminoglycoside(s) in the animal or patient is maintained at a minimum of 1–4 mg/L for at least about 1 hour and preferably no more than about 16 hours, more preferably no more than about 12 hours, most preferably no more than about 4–8 hours, after the administration of the gentamicin or other aminoglycoside(s), but the concentration of gentamicin or other aminoglycoside(s) in the animal or patient recedes to 1 mg/L or less than 1 mg/l at about 16 hours, preferably at about 12 hours, more preferably at about 4–8 hours, after the administration of the gentamicin or other aminogylcoside(s); and (ii) the concentration of the cephalosporin(s) or other antibacterial agent(s) acting at or near cell wall sites on pathogenic bacteria in the animal or patient is maintained at about 2 mg/l when the concentration of the gentamicin or other aminoglycoside(s) is maintained at or above 1–4 mg/l; optionally, the concentration of the cephalosporin(s) or other antibacterial agent(s) acting at or near cell wall sites on pathogenic bacteria, being maintained at about 2 mg/L for a further period of time of at least about 8–24 hours after the concentration of gentamicin or other aminoglycoside(s) declines to a negligible level.

In another embodiment, a method of using gentamicin or other aminoglycoside(s) in potentiating the action of a cephalosporin(s) or other antibacterial agent(s) acting at or near cell wall sites on pathogenic bacteria in the treatment of pathogenic bacterial infections in animals, particularly in the treatment of Gram-negative pathogenic bacterial infections in human patients is provided and comprises administering to the animal or patient, either separately or together, the gentamicin or other aminoglycoside(s) and the cephalosporin(s) or other antibacterial agent(s) acting at or near cell wall sites on pathogenic bacteria, such that:

(i) the concentration of gentamicin or other aminoglycoside(s) in the animal or patient is about 4–12 mg/L at about 30 minutes after the administration of the gentamicin or other aminoglycoside(s);

(ii) the concentration of gentamicin or other aminoglycoside(s) in the animal or patient is maintained at a minimum of 1–4 mg/l for at least about 1 hour and preferably no more than about the next 16 hours, more preferably no more than about the next 12 hours, most preferably no more than about the next 4–8 hours, after the administration of the gentamicin or other aminoglycoside(s), but the concentration of gentamicin or other aminoglycoside(s) in the animal or patient declines to 1 mg/l or less than 1 mg/l at about 16 hours, preferably at about 12 hours, more preferably at about 4–8 hours, after the administration of the gentamicin or other aminoglycoside(s); and (iii) the concentration of cephalosporin(s) or other antibacterial agents acting at or near cell wall sites on pathogenic bacteria, in the animal or patient is maintained at about 2 mg/l when the concentration of the gentamicin or other aminoglycoside(s) is maintained at or above 1–4 mg/l, optionally, the concentration of the cephalosporin(s) or other antibacterial agent(s) acting at or near cell wall sites on pathogenic bacteria, being maintained at about 2 mg/l for a further period of time of at least about 8–24 hours after the concentration of gentamicin or other aminoglycoside(s) declines to a negligible level.

A further embodiment of the present invention provides a composition suitable for the treatment of pathogenic bacterial infections in animals, particularly in the treatment of Gram-negative pathogenic bacterial infections in human patients, comprising:

(a) a cephalosporin(s) or other antibacterial agent(s) acting at or near cell wall sites on pathogenic bacteria; and (b) a potentiating amount of gentamicin or other aminoglycoside(s), wherein the composition is formulated to deliver to the animal or patient: (i) the gentamicin or other aminoglycoside(s) at a maintained concentration of a minimum of 1–4 mg/l for at least about 1 hour and preferably for no more than about 16 hours, more preferably no more than about 12 hours, most preferably no more than about 4–8 hours, after the administration of the composition to the animal or patient, but the concentration of gentamicin or other aminoglycoside(s) in the animal or patient recedes to 1 mg/l or less than 1 mg/l at about 16 hours, preferably at about 12 hours, more preferably at about 4–8 hours, after the administration of the gentamicin or other aminoglycoside(s); and (ii) the cephalosporin(s) or other antibacterial agent(s) acting at or near cell wall sites on pathogenic bacteria, at a maintained concentration of about 2 mg/l when the concentration of the gentamicin or other aminoglycoside(s) is maintained at or above 1–4 mg/l, optionally, the composition further delivering to the animal or patient, the cephalosporin(s) or other antibacterial agent(s) acting at or near cell wall sites on pathogenic bacteria, at a maintained concentration of about 2 mg/l for a further period of time of at least about 8–24 hours after the concentration of gentamicin or other aminoglycoside(s) declines to a negligible level.

In yet another embodiment, the present invention provides a composition suitable for the treatment of pathogenic bacterial infections in animals, particularly in the treatment of Gram-negative pathogenic bacterial infections in human patients, comprising:

(a) a cephalosporin(s) or other antibacterial agent(s) acting at or near cell wall sites on pathogenic bacteria; and (b) a potentiating amount of gentamicin or other aminoglycoside(s), wherein the composition is formulated to deliver to the animal or patient: (i) the gentamicin or other aminoglycoside(s) at a concentration of about 4–18 mg/l at about 30–240 minutes after the administration of the composition to the animal or patient; (ii) the gentamicin or other aminoglycoside(s) at a maintained concentration of a minimum of 1–4 mg/l for at least about 1 hour and preferably for no more than about 16 hours, more preferably no more than about 12 hours, most preferably no more than about 4–8 hours, after the administration of the composition to the animal or patient, but the concentration of gentamicin or other aminoglycoside(s) in the animal or patient recedes to 1 mg/l or less than 1 mg/l at about 16 hours, preferably at about 12 hours, more preferably at about 4–8 hours, after the administration of the gentamicin or other aminoglycoside(s); and (iii) the cephalosporin(s) or other antibacterial agent(s) acting at or near cell wall sites on pathogenic bacteria, at a maintained concentration of about 2 mg/l when the concentration of the gentamicin or other aminoglycoside(s) is maintained at or above 1–4 mg/l, optionally, the composition further delivering to the animal or patient, the cephalosporin(s) or other antibacterial agent(s) acting at or near cell wall sites on pathogenic bacteria, at a maintained concentration of about 2 mg/l for a further period of time of at least about 8–24 hours after the concentration of gentamicin or other aminoglycoside(s) declines to a negligible level.

In summary, the invention provides a method of potentiating the activity of antibacterial agents that act on bacterial cell walls so as to provide a complete killing effect in all body sites including the bloodstream, tissues, tissue spaces and organs.

In a 24 hour period, the invention includes the initial step of simultaneous administration of defined doses of an antibacterial agent with defined doses of aminoglycoside, but with provision for reduction, or cessation, of the aminoglycoside dose rate some 8–16 hours later (so as to allow removal of the aminoglycoside from the body, thus avoiding the toxic effects of aminoglycoside on kidney function, hearing, posture and balance) while the administration of the surface-acting antibacterial agent is preferably continued.

The aminoglycoside target concentration is most preferably a peak of no less than the microbiological equivalent of a gentamicin and tobramycin concentration of 3–4 mg/L, maintained for no less than 1 hour. Exposure to peak concentrations of up to the equivalent for 18 mg/L of gentamicin/tobramycin are provided for where resistant organisms are detected or suspected. The concentration of surface acting antibacterial agent is preferably no less than the microbiological equivalent of cephazolin at 2 mg/L.

Although the invention has been described in detail for the purposes of clarity and understanding, it will be apparent to the person skilled in the art that various modifications and/or additions may be incorporated in the invention without departing from the spirit and scope thereof as described.

TABLE 1

| Gentamicin Post-Distribution Peak followed by main-tained cephazolin concentrations | | Bacterial Counts [log 10 cfu/mL] | | | |
|---|---|---|---|---|---|
| | | −0.5 h | 2 h | 8 h | 24 h |
| 8 mg/L bolus gentamicin | 0 mg/L | 5.87 ± 0.35 | 1.32 ± 0.69 | 4.91 ± 0.70 | 8.88 ± 0.11 |
| followed by a cephazolin | 0.5 mg/L | 5.86 ± 0.05 | 2.53 ± 2.01 | 5.28 ± 0.65 | 8.94 ± 0.09 |
| trough of: | 1.0 mg/L | 6.06 ± 0.08 | 1.43 ± 0.87 | 5.57 ± 0.59 | 8.97 ± 0.20 |
| | 2.0 mg/L | 6.00 ± 0.14 | 0.98 ± 0.78 | 2.87 ± 0.40 | 6.24 ± 0.66 |
| | 4.0 mg/L | 6.02 ± 0.07 | 0.65 ± 0.71 | NGD | NGD |
| 12 mg/L bolus gentamicin | 0 mg/L | 6.10 ± 0.26 | 0.69 ± 0.87 | 4.54 ± 1.15 | 8.80 ± 0.05 |
| followed by a cephazolin | 0.5 mg/L | 5.87 ± 0.04 | 0.48 ± 0.76 | 4.66 ± 0.95 | 8.81 ± 0.06 |
| trough of: | 1.0 mg/L | 5.94 ± 0.10 | 0.43 ± 0.67 | 1.16 ± 1.34 | 8.33 ± 1.10 |
| | 2.0 mg/L | 5.93 ± 0.20 | 0.22 ± 0.53 | NGD | NGD |
| | 4.0 mg/L | 5.95 ± 0.09 | 0.22 ± 0.53 | NGD | NGD |
| 16 mg/L bolus gentamicin | 0 mg/L | 5.85 ± 0.050 | 0.48 ± 0.76 | 3.85 ± 1.24 | 8.79 ± 0.05 |
| followed by a cephazolin | 0.5 mg/L | 5.78 ± 0.028 | NGD | 3.81 ± 0.91 | 8.84 ± 0.03 |
| trough of: | 1.0 mg/L | 5.88 ± 0.030 | 0.22 ± 0.53 | 1.12 ± 1.25 | 8.82 ± 0.04 |
| | 2.0 mg/L | 5.83 ± 0.030 | NGD | NGD | NGD |
| | 4.0 mg/L | 5.89 ± 0.030 | NGD | NGD | NGD |
| 20 mg/L bolus gentamicin | 0 mg/L | 5.89 ± 0.03 | NGD | 3.15 ± 0.734 | 8.81 ± 0.04 |
| followed by a cephazolin | 0.5 mg/L | 5.87 ± 0.06 | NGD | 2.95 ± 1.38 | 8.79 ± 0.05 |
| trough of: | 1.0 mg/L | 5.85 ± 0.03 | NGD | 0.64 ± 1.07 | 5.73 ± 3.66 |
| | 2.0 mg/L | 5.87 ± 0.05 | NGD | NGD | NGD |
| | 4.0 mg/L | 5.87 ± 0.04 | NGD | NGD | NGD |

TABLE 2

| Maintained Cephazolin | Bacterial Count [log 10 $\mu$/mL] | | | |
|---|---|---|---|---|
| Concentrations | 0 h | 2 h | 8 h | 24 h |
| Control | 5.91 ± 0.10 | 7.36 ± 0.45 | 8.76 ± 0.07 | 8.84 ± 0.06 |
| 0.5 mg/L | 5.88 ± 0.09 | 7.43 ± 0.28 | 8.67 ± 0.24 | 8.82 ± 0.06 |
| 1.0 mg/L | 5.83 ± 0.29 | 6.21 ± 0.76 | 8.59 ± 0.35 | 8.79 ± 0.05 |
| 2.0 mg/L | 5.88 ± 0.07 | 3.70 ± 0.32 | 4.98 ± 0.34 | 8.79 ± 0.05 |
| 4.0 mg/L | 5.88 ± 0.06 | 3.61 ± 0.22 | 4.38 ± 0.42 | 6.14 ± 0.93 |
| 12.5 mg/L | 5.85 ± 0.14 | 3.11 ± 0.26 | 2.18 ± 0.63 | 4.77 ± 1.89 |
| 50 mg/L | 5.93 ± 0.11 | 2.17 ± 0.39 | 1.55 ± 0.93 | 1.56 ± 1.14 |
| 75 mg/L | 5.82 ± 0.23 | 2.09 ± 0.29 | 1.11 ± 0.96 | 1.05 ± 1.23 |
| 100 mg/L | 5.85 ± 0.08 | 2.01 ± 0.26 | 0.86 ± 0.95 | 0.70 ± 0.78 |
| 200 mg/L | 5.86 ± 0.04 | 2.16 ± 0.24 | 0.78 ± 0.87 | 1.43 ± 0.74 |
| 250 mg/L | 5.81 ± 0.03 | 1.82 ± 0.44 | 1.22 ± 0.96 | 1.61 ± 0.86 |

TABLE 3

| Gentamicin Profile | $C_{max}$ (mg/liter) | $C_{min}$ (mg/liter) | $AUC_{0-49\,h}$ (mg · hr/liter) | BACTERIAL COUNTS log$^{10}$ (CFU/mL) | | | |
|---|---|---|---|---|---|---|---|
| | | | | 3 hr | 11 hr | 25 hr | 49 hr |
| *Post-distribution peak of 4 mg/liter then reconstituted at 1 hr to: | | | | | | | |
| 0 mg/liter | 6.22 ± 0.33 | 0 | 3.97 ± 0.09 | 3.96 ± 0.70 | 9.24 ± 0.34 | 9.15 ± 0.17 | 8.93 ± 0.12 |
| 2.0 mg/liter | 6.32 ± 0.25 | 1.93 ± 0.24 | 102.66 ± 6.91 | 1.92 ± 1.21 NS | 7.76 ± 1.06 p = 0.01 | 8.69 ± 0.63 NS | 9.34 ± 0.27 NS |
| 2.5 mg/liter | 6.23 ± 0.23 | 2.47 ± 0.31 | 124.40 ± 4.27 | 0.33 ± 0.52 p = 0.01 | 0.33 ± 0.52 p = 0.01 | 4.85 ± 3.82 p = 0.01 | 5.98 ± 4.63 NS |
| 3.0 mg/liter | 6.28 ± 0.37 | 2.88 ± 0.23 | 153.43 ± 11.01 | 0.33 ± 0.52 p = 0.01 | NGD p < 0.01 | NGD p < 0.01 | NGD p < 0.01 |
| **Post-distribution peak of 4 mg/liter then reconstituting to 3.0 mg/liter at 1 hr and maintaining for: | | | | | | | |
| 0 hr (control) | 6.12 ± 0.35 | 0 | 3.93 ± 0.33 | 3.05 ± 0.33 | 8.89 ± 0.20 | 9.07 ± 0.12 | 9.01 ± 0.06 |
| 2 hr | 6.23 ± 0.27 | 2.45 ± 0.24 | 124.98 ± 3.08 | 0.17 ± 0.41 p < 0.01 | 0.55 ± 0.61 p = 0.01 | 7.95 ± 0.54 p = 0.01 | 8.89 ± 0.19 NS |
| 4 hr | 6.30 ± 0.45 | 2.37 ± 0.34 | 120.99 ± 6.05 | 0.17 ± 0.41 p < 0.01 | 0.17 ± 0.41 p < 0.01 | 5.18 ± 4.02 p = 0.01 | 5.99 ± 4.64 p = 0.03 |
| 8 hr | 6.37 ± 0.22 | 2.35 ± 0.19 | 119.78 ± 8.84 | 0.33 ± 0.52 p < 0.01 | NGD p < 0.01 | NGD p < 0.01 | NGD p < 0.01 |

TABLE 4

| Exposure time to maintained concentration of gentamicin | Trough gentamicin concentration in broth | | | | | |
|---|---|---|---|---|---|---|
| | 0 mg/L | 0.5 mg/L | 1.0 mg/L | 2.0 mg/L | 3.0 mg/L | 4.0 mg/L |
| 1 hr | + | + | − | − | − | − |
| 2 hr | + | + | − | − | − | − |
| 3 hr | + | + | − | − | − | − |
| 4 hr | ++ | + | − | − | − | − |
| 8 hr | +++ | ++ | − | − | − | − |
| 24 hr | +++ | +++ | − | − | − | − |
| 48 hr | +++ | +++ | − | − | − | − |

The claims defining the invention are as follows:

1. An in vivo method of potentiating the activity of an antibacterial agent active on bacterial cell wall, comprising the steps of:
   (a) exposing said bacterial cell wall to an aminoglycoside in an amount effective to attain a peak concentration of 4 to 14 mg/l and thereafter maintaining the concentration substantially between 0.05 mg/l to 4 mg/l for at least 1 hour; and
   (b) exposing said bacterial cell wall to a single dose of said antibacterial agent wherein the concentration of the antibacterial agent is maintained at a concentration of at least 2 mg/l, while the concentration of the aminoglycoside declines.

2. A method according to claim 1, wherein the aminoglycoside concentration peaks at 30–240 minutes after administration of said aminoglycoside.

3. A method according to claim 1, wherein the concentration of the aminoglycoside is maintained at 1–4 mg/l for up to 16 hours.

4. A method according to claim 1, wherein the concentration of the aminoglycoside is maintained at 1 mg/l or less than 1 mg/l for up to 24 hours.

5. A method according to claim 1, wherein the antibacterial agent is maintained at 2 mg/l or more when the aminoglycoside is maintained at 1–4 mg/l and optionally, for a further 8–24 hours thereafter.

6. A method according to claim 1, wherein the antibacterial agent active on bacterial cell wall comprises a cephalosporin or cephamycin.

7. A method according to claim 6, wherein the antibacterial agent is selected from the group consisting of cephalosporin, cephalothin, cephaloridine, cephalexin, cephaglycine, cephradine, cefaclor, cefoxitin, cefamandole, cefotaxime, ceftriaxone, ceftazidime and cefotetan.

8. A method according to claim 1, wherein the antibacterial gent active on bacterial cell wall is a β-lactam antibiotic.

9. A method according to claim 1, wherein the aminoglycoside is selected from the group consisting of gentamicin, tobramycin, netilimicin, amikacin and streptomycin.

10. A method according to claim 1, wherein the bacterial infection is caused by bacteria selected from the group consisting of Gram-positive bacteria, Gram-negative bacteria and mycobacteria.

11. A method according to claim 1, wherein the concentration of the antibacterial agent is maintained at about 2 mg/l while the aminoglycoside concentration is maintained at or above 1 or 4 mg/l.

12. A method according to claim 11, wherein the concentration of the antibacterial agent is maintained at about 2 mg/l for at least about 8 to 24 hours after the concentration of the aminoglycoside declines to a negligible level.

* * * * *